US006482854B1

(12) United States Patent
Lipton et al.

(10) Patent No.: US 6,482,854 B1
(45) Date of Patent: Nov. 19, 2002

(54) GLAUCOMA TREATMENT

(75) Inventors: Stuart A. Lipton; Evan B. Dreyer, both of Newton, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 09/276,305

(22) Filed: Mar. 25, 1999

(51) Int. Cl.⁷ .............................................. A61K 31/275
(52) U.S. Cl. ...................................... 514/523; 514/912
(58) Field of Search ................................ 514/523, 912

(56) References Cited

U.S. PATENT DOCUMENTS

| | | | |
|---|---|---|---|
| 4,158,005 A | 6/1979 | Bodor et al. | |
| 4,396,625 A | 8/1983 | Yamamori et al. | |
| 4,425,346 A | 1/1984 | Horlington | |
| 4,981,871 A | 1/1991 | Abelson | |
| 5,017,579 A | 5/1991 | Gubin et al. | |
| 5,070,088 A | 12/1991 | Atwal et al. | |
| 5,075,440 A | * 12/1991 | Wustrow | 540/468 |
| 5,376,676 A | * 12/1994 | Lee | 514/473 |
| 5,435,998 A | 7/1995 | Abelson | 424/78.04 |
| 5,500,230 A | * 3/1996 | Nathanson | 424/619 |

FOREIGN PATENT DOCUMENTS

| | | |
|---|---|---|
| WO | WO 88/05306 | 7/1988 |
| WO | WO 93/23082 A | 11/1993 |
| WO | WO 94/06428 A | 3/1994 |

OTHER PUBLICATIONS

Dreyer et al., Excitatory Aminoacids in Glaucoma: A Potentially Novel Etiology of Neuronal Loss in this Optic Neuropathy, Society for Neuroscience Abstracts 18:439 (1992).
Dreyer et al., A Proposed Role for Excitatory AMino Acids in Glaucoma Viral Loss, Investigative Opthalmology and Visual Science 34:1504 (1993).
Nathanson, Nitrovasodilators as a New Class of Ocular Hypotensive Agents, Journal of Pharmacology and Experimental Therapeutics 260:961 (1992).
Dreyer, Amino Acid Analysis of Vitreous Specimens in Patients with Open Angle Glaucoma, Ophthalmol. Visual Science 32:871 (1991).
Sommer et al., Tips 13:291–296, 1992.
Sucher et al., The Journal of Neuroscience 11:966–971, 1991.
Sucher et al., Brain Research 297:297–302, 1991.
Nakanishi, Science 258:597–603,1992.
Meldrum et al., Tips 11:379–387, 1990.
Moriyoshi et al., Nature 354:31–37, 1991.
Finkelstein et al., British J. of Ophthalmology, 74:280–282, 1990.
Watkins et al., Tips 11:25–33, 1990.
Hess, Annu. Rev. Neurosci. 13:337–56, 1990.
Levy et al., Neurology 40:852–855, 1990.
Faden et al., Science 244:798–800, 1989.
Karschin et al., J. of Physiology 418:379–396, 1989.
Bean, Annu. Rev. Physiol. 51:367–384, 1989.
Hahn et al., Proc. Natl. Sci. USA 85:6556–6560, 1988.
Lipton et al., J. Physiol 385:361–391, 1987.
Svenneby et al., Biochemical Society Transactions 15:213–215, 1987.
Rosenthal, Amer. J. Ophthalmology 102:570–574, 1986.
Sisk et al., Graefe's Archive Clin. Exp. Ophthalmol. 223:250–258, 1985.
Hannappel et al., Ophthalmic Res. 17:341–343, 1985.
Ehlers, Acta Ophthalmologic 59:576–586, 1981.
Quigley et al., Arch Ophthalmol 99:635–649, 1981.
Quigley et al., Invest. Ophthalmol. Vis. Sci. 19:505–517, 1980.
Schonheyder et al., Acta Ophthalmologica 53:627–634, 1975.
Hayreh, Brit. J. Ophthal. 58:863–876, 1974.
Ehlers et al., Acta Ophthalmologica, Jun. 1973.
Durham et al., Clinical Chemistry 17:285–289, 1971.
Durham, Tr. Am. Ophth. Soc., 68:462–500, 1970.
Olney, J. Neuropathology Exp. Neurology, IIVIII:455–474, 1969.
Dickinson et al., Investigative Ophthalmolgy, 7:551–563, 1968.
Lucas et al., A.M. A. Archives of Ophthalmology, 58:193–201, 1957.

* cited by examiner

*Primary Examiner*—Zohreh Fay
(74) *Attorney, Agent, or Firm*—Fish & Richardson P.C.

(57) ABSTRACT

Elevated glutamate levels are associated with glaucoma, and damage to retinal ganglion cells can be controlled by administering to the patient a compound capable of reducing glutamate induced excitotoxicity in a concentration effective to cause reduction of such excitotoxicity.

9 Claims, 1 Drawing Sheet

GLAUCOMA TREATMENT

This application relates to glaucoma treatment.

This application is a continuation and claims the benefit of priority under 35 USC §120 of U.S. application Ser. No. 07/984,939, filed Dec. 4, 1992. This application is hereby incorporated by reference in it's entirety.

BACKGROUND OF THE INVENTION

Glaucoma affects approximately five percent of persons who are older than 65 years and fourteen percent of those older than 80 years. The visual loss which results from glaucoma conditions has been attributed to progressive damage of the optic nerve and consequent loss of retinal ganglion cells, mediated by elevated intraocular pressure (Quigley et al., *Invest. Ophthalmol. Vis. Sci.* 19:505, 1980). Consequently, therapeutic modalities have focused on the management of intraocular pressure.

Many compounds have been proposed to treat glaucoma. See generally, Horlington U.S. Pat. No. 4,425,346; Komuro et al. U.S. Pat. No. 4,396,625; Gubin et al. U.S. Pat. No. 5,017,579; Yamamori et al. U.S. Pat. No. 4,396,625; and Bodor et al. U.S. Pat. No. 4,158,005.

At the present time, medical control of intraocular pressure consists of topical or oral administration of a miotic (e.g., pilocarpine), epinephrine derivatives (e.g., dipivalyl epinephrine), or topical beta blockers (e.g., timolol). Abelson U.S. Pat. No. 4,981,871 discloses the use of a class I voltage-dependent $Ca^{++}$ channel blocking agent (a phenylalkylamine) to treat elevated ocular pressure (Specifically, Abelson '871 discloses the use of verapamil, which does not cross the blood brain barrier and does not reach retinal ganglion cells).

Miotics may reduce the patient's visual acuity, particularly in the presence of lenticular opacities. Topical beta blockers such as Timolo™ have been associated with systemic side effects such as fatigue, confusion, or asthma, and exacerbation of cardiac symptoms has been reported after rapid withdrawal of topical beta blockers. Oral administration of carbonic anhydrase inhibitors, such as acetazolamide, may also be used, but these agents can be associated with systemic side effects including chronic metabolic acidosis.

If current methods of treatment fail to reduce intraocular pressure, laser treatment or a drainage operation (e.g., trabeculectomy) is usually performed.

SUMMARY OF THE INVENTION

We have discovered that glaucoma is associated with elevated glutamate. We have further discovered that glaucoma management, particularly protection of retinal ganglion cells, can be achieved by administering to the patient a compound capable of reducing glutamate-induced excitotoxicity in a concentration effective to reduce such excitotoxicity, thereby reducing the loss of retinal ganglion cells resulting from such excitotoxicity.

By way of additional background underlying the invention, excessive influx of $Ca^{2+}$ due to glutamate-mediated receptor activation is thought to underlie excitotoxicity. Several types of calcium-permeable ion channels that can be involved in this excitotoxicity are mentioned below, including voltage-dependent $Ca^{2+}$ channels, the NMDA receptor channel complex, and other channels directly coupled to glutamate (or excitatory amino acid) receptors. Such channels are reviewed in Sommer, B. and Seeburg, P. H. Glutamate receptor channels: novel properties and new clones. Trends Pharmacological Sciences 13:291–296 (1992); Nakanishi, S. Molecular Diversity of glutamate receptors and implications for brain function. Science 248:597–603 (1992).

One aspect of the invention generally features administering antagonists of glutamate-induced excitotoxicity that are capable of crossing both the blood-brain brain barrier and the blood-retina barrier to human patients with non-vascular glaucoma—i.e., all types of glaucoma other than the type commonly termed "neo-vascular" glaucoma.

A second aspect of the invention features the use of antagonists that do not have a substantial direct effect on glutamate toxicity mediated by the L-type voltage dependent $Ca^{++}$ channel, but instead affect glutamate toxicity mediated by other mechanisms detailed below. We consider that a compound has a substantial direct effect on glutamate toxicity mediated by the L-type voltage dependent $Ca^{++}$ channel if it produces a statistically significant result in experiments measuring glutamate induced effects by the general method described in Karschian and Lipton, *J. Physiol.* 418: 379–396 (1989) or by other techniques for measuring antagonism of the L-type $Ca^{++}$ channel known to those in the art. (We contrast the direct effect so measured with the secondary effects of excitotoxicity mediated by other channels, which in turn causes flow through the voltage dependent $Ca^{++}$ channels.) In particular, this aspect of the invention features use of compounds which are not Class I voltage dependent $Ca^{++}$ channel antagonists, e.g., compounds that are not phenylalkylamines. Preferably, this second aspect of the invention features antagonists of the N-methyl-D-aspartate (NMDA) receptor channel complex and other glutamate receptor antagonists described in detail below. Other useful compounds according to the invention include antagonists of non-NMDA receptors—i.e. antagonists of glutamate induced excitotoxicity that do substantially affect excitotoxicity mediated via the NMDA receptor channel complex (e.g., excitotoxicity caused by NMDA in experiments well known to those in the art), but instead operate by antagonizing excitotoxicity mediated via other glutamate receptors. Also, antagonists of the second aspect are used in preferred embodiments of the first aspect of the invention.

According to both aspects, the invention preferably will be used to treat patients which have primary open-angle glaucoma, chronic closed-angle glaucoma, pseudoexfoliation, or other sub-types of glaucoma or ocular hypertension. Preferably, the agent is administered over an extended period (e.g., at least six months and preferably at least one year), regardless of changes in the patient's intraocular pressure over the period of administration.

Particularly preferred compounds used in both aspects of the invention are antagonists of the NMDA receptor-channel complex. The term "NMDA receptor antagonists" includes several sub-types of NMDA antagonists including: a) channel blockers—i.e., antagonists that operate uncompetitively to block the NMDA receptor channel; b) receptor antagonists—antagonists that compete with NMDA to act at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation, such as agents that inhibit activation of protein kinase C activation by NMDA stimulation, antioxidants, and agents that decrease phosphatidylinositol metabolism.

Other compounds that are useful in the invention include voltage-dependent calcium channel antagonists which are described in greater detail below, particularly those which cross the blood-brain and blood-retina barriers and which can be administered chronically. Other preferred agents act as antagonists of non-NMDA receptors (glutamate receptor types other than the NMDA receptor complex discussed above), and include agents which block ionotropic glutamate receptors or interact with metabotropic glutamate receptors (Nakanishi, supra). Other preferred agents act to limit (reduce) release of glutamate from cells, thereby acting upstream from the glutamate receptors in the excitatory neurotoxicity process. Still other agents may act by blocking downstream effects of glutamate receptor stimulation, e.g., the intracellular consequences of glutamate interaction with a cell membrane glutamate receptor, such as agents (like dantrolene) that block the rise in intracellular calcium following stimulation of membrane glutamate receptors.

The most preferred compounds are those capable of crossing the blood-brain barrier or the blood-retinal barrier; these compounds may be administered orally, intravenously, or topically and cross intervening barriers including the blood brain barrier to reach the retinal ganglion cells. Compounds that do not freely cross the blood-brain barrier are less preferred; these compounds may be administered intravitreally to the retina. In the case of compounds that have an intermediate ability to cross the blood-brain barrier, the mode of administration will depend on the dosage required and other factors.

Among the preferred compounds are amantadine derivatives (e.g., memantine, amantadine, and rimantadine), nitroglycerin, dextorphan, dextromethorphan, and CGS-19755. See generally, the compounds listed in Table 2.

The invention is useful for the reduction or prevention (including prophylactic treatment) of damage to retinal ganglion cells and their axons comprising the optic nerve in patients with glaucoma.

Other features and advantages of the invention will be apparent from the following description of the preferred embodiment thereof, and from the claims.

DESCRIPTION OF THE PREFERRED EMBODIMENTS

The drawings will first be briefly described.
Drawings

Following is a detailed description indicating that increased levels of glutamate in the vitreous is associated with glaucoma mediated damage of the optic nerve. We do not wish to bind ourselves to a specific theory. However, in view of well documented literature establishing the excitotoxic effect of glutamate on neurons of the central nervous systems, including retinal neurons, it is likely that the compounds of the invention are useful for treating glaucoma because of their ability to block glutamate induced excitoxicity. Also outlined are assays which provide one skilled in the art with the necessary guidance to determine the potential efficacy of receptor antagonists in reducing or preventing damage of the retinal ganglion cells.

Detection of Vitreal Levels of Glutamate

Vitreous samples from twenty-six glaucomatous and non-glaucomatous patients (on the General Eye and Glaucoma Consultation Services of the Massachusetts Eye and Ear Infirmary) were assayed. Samples were centrifuged at high speed in a Microfuge for 60 minutes at 4° C. The supernatant was then immediately frozen in liquid nitrogen and stored at −80° C. until assayed for amino acid concentration. Amino acid analyses were performed by the Neurochemistry Laboratory of the Massachusetts General Hospital. Immediately before analysis, salicylic acid was added to each sample. Analyses were carried out by cation exchange on a Beckmann Amino Acid Analyzer (model 6300), as described in detail previously (Lipton, et al. *Neuron*, 7:11, 1991). Duplicate analyses of samples from three controls with cataract and three patients with glaucoma were performed by the Amino Acid Laboratory at Children's Hospital of Boston. These duplicate values agreed in all cases within 9% of the results obtained at the Massachusetts General Hospital laboratory.

Samples were obtained from fifteen patients with documented glaucoma and cataract, and from eleven patients with cataract alone. Each patient with glaucoma (either primary open angle, chronic angle closure, or pseudoexfoliation) had either been on anti-glaucoma therapy for at least one year prior to cataract surgery, or had undergone a filtering operation for pressure control.

Figure 1:
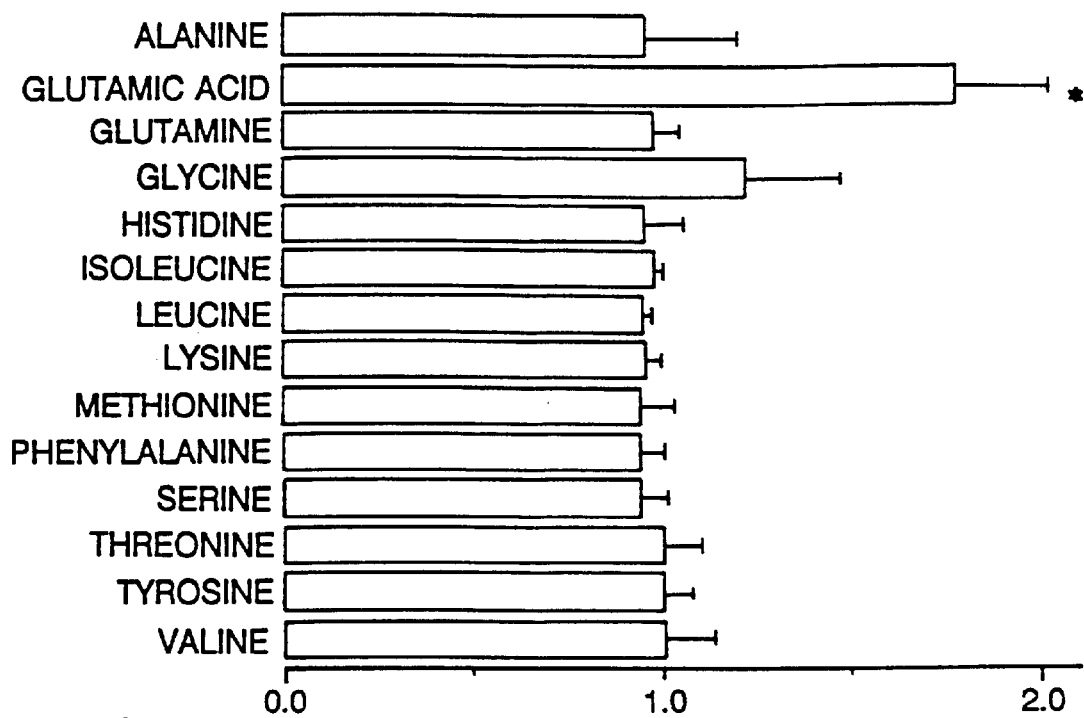
FIG. 1 is a bar graph of normalized amino acid concentrations in glaucomatous vitreous when compared to control vitreous.

Amino acid analyses reveal an approximately two-fold elevation in glutamic acid levels in patients with glaucoma and cataract when compared to cataractous controls (FIG. 1 and Table 1). Data were analyzed by the students' t test and were significant at $p<0.0001$. Apart from glutamate, no other statistically significant variation in amino acid concentrations was detected in these patients. The data were further stratified by patient age, axial length of the eye, sex, race, type or severity of cataract (as judged preoperatively), etiology of glaucoma, or type of anti-glaucoma therapy. The presence and severity of cataract (based upon pre-operative examination and cataract type) were similar between the control and glaucoma groups. Thus the group of patients with cataract alone could serve as an appropriate control group.

TABLE 1

Amino Acid Concentrations in Vitreous of Control and Glaucoma Patients

| Amino Acid:* | Controls: | Glaucoma: |
| --- | --- | --- |
| Alanine | 167.4 ± 44.3 | 159.1 ± 50.7 |
| Aspartate | Not Detectable† | Not Detectable† |
| Glutamic Acid | 12.6 ± 1.8 | 22.3 ± 2.8‡ |
| Glutamine | 479.0 ± 33.1 | 466.1 ± 41.1 |
| Glycine | 22.9 ± 5.0 | 27.6 ± 22.9 |
| Histidine | 34.2 ± 3.7 | 32.5 ± 3.3 |
| Isoleucine | 35.1 ± 1.2 | 34.1 ± 4.4 |
| Leucine | 77.9 ± 2.5 | 73.6 ± 7.9 |
| Lysine | 106.3 ± 4.6 | 101.5 ± 7.7 |
| Methionine | 21.5 ± 2.2 | 20.1 ± 2.9 |
| Phenylalanine | 63.4 ± 4.7 | 58.9 ± 6.9 |
| Serine | 105.5 ± 8.7 | 98.6 ± 7.6 |
| Threonine | 57.5 ± 6.5 | 56.8 ± 7.3 |
| Tyrosine | 15.8 ± 1.3 | 15.6 ± 1.2 |
| Valine | 143.6 ± 19.1 | 143.2 ± 19.4 |

(*) All concentrations are μmols/liter ± standard deviation; those amino acids not tabulated were not analyzed.
(†) Below 5 μmols/liter.
(‡) When compared to control, significant by the students' t test at $P < 0.0001$.

Figure 2:
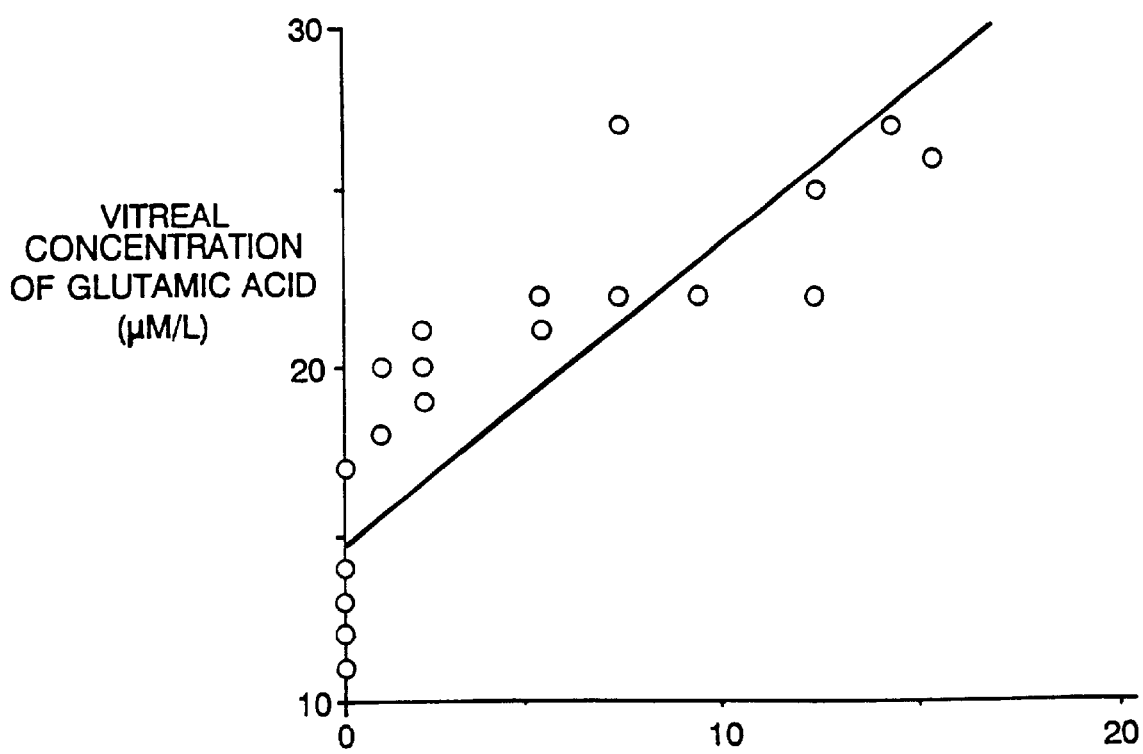
FIG. 2 is a graph of amino acid concentration of glutamate in vitreous plotted as a function of years of glaucoma.

The glutamate concentrations detected in these patients were also plotted as a function of time from the diagnosed onset of the disease with patients having cataract alone plotted at time zero. A graph of these data is shown in FIG. 2. The correlation coefficient for the line drawn is $r=0.702$. Thus, although elevated in all glaucomatous vitreous assayed, there is a direct correlation between the level of glutamate and the stage of visual loss from glaucoma.

The elevated glutamate can damage neurons by NMDA-mediated activation; and glutamate (or congener) activation of non-NMDA receptors could also contribute to retinal ganglion cell loss, and may be important to control, even if the NMDA contribution predominates. See, generally, Sucher et al. *J. Neurosci.,* 11:966 (1991).

One explanation for the toxic level of glutamate found in glaucomatous vitreous is that it is released by dying cells during the course of the destruction occasioned by the glaucomatous process. For example, other forms of trauma to nerve cells are known to lead to the accumulation of extracellular glutamate (Faden et al. *Science,* 244:798–800 (1989)), and the elevated pressure of the glaucomatous process could exert traumatic injury on cells. The glutamate thereby released could, in turn, lead directly to further neuronal injury. A second possibility is that the glaucomatous process (perhaps through elevated pressure on the cell soma) leads to increased permeability of damaged retinal cells, exposing intracellular stores of glutaminase. This might promote the conversion of glutamine to glutamate. However, whatever the mechanism of generation, this neurotoxin is elevated in the glaucomatous population, and therefore participates in the destruction of retinal ganglion cells and the consequent visual loss seen in this disease.

Selection of Antagonists

In view of our discovery that such excitotoxicity is associated with glaucoma, the invention features antagonists having certain specific characteristics: the ability to cross the blood-brain and blood-retina barriers; and the ability to be administered chronically, even when intraocular pressure has been controlled to within normal ranges. Within those guidelines, any suitable antagonist of the glutamate induced exitotoxicity may be used in accordance with the invention. As mentioned, in preferred embodiments, N-methyl-D-aspartate (NMDA) subtype of glutamate receptor-channel complex may be used to reduce or prevent glaucoma related injury to the retinal ganglion cells and their axons comprising the optic nerve with consequent vision loss. Many antagonists of the NMDA receptor have been identified (Watkins et al., Trends in Pharmacological Sci. 11:25, 1990, hereby incorporated by reference). There are several recognized sub-types of NMDA receptor including: a) channel blockers—i.e., antagonists that operate non-competitively to block the NMDA receptor channel; b) receptor antagonists—antagonists that compete with NMDA, acting at the NMDA binding site; c) agents acting at either the glycine co-agonist site or any of several modulation sites such as the zinc site, the magnesium site, the redox modulatory site, or the polyamine site; d) agents which inhibit the downstream effects of NMDA receptor stimulation such as agents that inhibit activation of protein kinase C activation by NMDA stimulation, antioxidants, and agents that decrease phosphatidylinositol metabolism.

Other compounds that are useful in this invention include: other non-NMDA receptor antagonists, such as agents which block other types of ionotropic glutamate receptors or interact with metabotropic glutamate receptors; voltage-dependent calcium channel antagonists (against L, N, T, and P type channels) (Bean, B. P. Annu. Rev. Physiol. 51:367–384 (1989); Hess, P. Annu. Rev. Neurosci. 13:337–356 (1990)), and are described in greater detail below; and agents which act to decrease the release of glutamate, thereby acting upstream in the excitatory neurotoxicity process.

Table 2, below lists various suitable NMDA and non-NMDA receptors which do not operate via the voltage-dependent $Ca^{++}$ ion channel. Tables 3–5 list antagonists of the voltage dependent $Ca^{++}$ channel, which can be used by themselves in connection with the first aspect of the invention, and which can also be used in combination with other antagonists in the second aspect of the invention.

TABLE 2

| NMDA Antagonists | NMDA Antagonists | NMDA Antagonists |
| --- | --- | --- |
| 1. Competitive NMDA Antagonists (act at agonist binding site) | 2. Channel Blockers (Un-Competitive NMDA Antagonists) | 3. Antagonists at Glycine Site of the NMDA Receptor |
| CGS-19755 (CIBA-GEIGY) and other piperidine derivatives, D-2-amino-5-phosphovalerate, D-2-amino-7-phosphonoheptanoate (AP7) | MK-801 (Dizocilpine) and other derivatives of dibenzyocycloheptene (Merck) | Kynurenate, 7-chloro-kynurenate, 5,7-chloro-kynurenate, thio-derivatives, and other derivatives. (Merck) |
| CPP [{3-2-carboxypiperazin-4-y-propyl-1-phosphonic acid]} | Sigma receptor ligands, e.g. Dextrorphan, dextromethorphan and morphinan derivatives (Hoffman La Roche) such as caramiphen and rimcazole (which also block calcium channels) | Indole-2-carboxylic acid |
| LY 274614, CGP39551, CGP37849, LY233053, LY233536 | Ketamine, Tiletamine and other cyclohexanes | DNQX |
| O-phosphohomoserine | Phencyclidine (PCP) and derivatives, and pyrazine compounds | Quinoxaline or oxidiazole derivatives including CNQX, NBQX |
| MDL 100,453 | Memantine, amantadine, rimantadine and derivatives | Glycine partial agonist (e.g. Hoecht-Roussel P-9939) |
| | CNS 1102 (and related bi- and tri-substituted guanidines) | |
| | Diamines | |
| | Conantokan peptide from Conus geographus | |
| | Agatoxin-489 | |
| | | 6. Other Non-Competitve NMDA Antagonists |
| 4. Polyamine Site of NMDA Receptor | 5. Redox Site of NMDA Receptor | |
| Arcaine and related biguanidines and biogenic polyamines | Oxidized and reduced glutathione | Hoechst 831917189 |
| Ifenprodil and related drugs | PQQ (pyrroloquinoline quinone) | SKB Carvedilol |
| Diethylenetriamine SL 82,0715 | Compounds that generate Nitric Oxide (NO) | |

TABLE 2-continued

| | | |
|---|---|---|
| 1,10-diaminodecane (and related inverse agonists) | or other oxidation states of nitrogen monoxide (NO+, NO−) including those listed in the box below<br>Nitroglycerin and derivatives, Sodium Nitroprusside, and other NO generating listed on p. 5 of this table<br>Nitric oxide synthase (NOS) Inhibitors: Arginine analogs including N -mono-methyl-L-arginine (NMA); N - amino-L-arginine (NAA); N -nitro-L-arginine (NNA); N - nitro-L-arginine methyl ester; N-iminoethyl-L-ornithine<br>Flavin Inhibitors: diphenyliodinium;<br>Calmodulia inhibitors, trifluoperizine<br>Calcineurin Inhibitors, e.g., FK-506 (Inhibits calcineurin and thus NOS diphosphorylase) | |

| Inhibitors of Downstream Effects of NMDA | Inhibitors of Downstream Effects of NMDA | Non-NMDA Receptor Antagonists |
|---|---|---|
| 7. Agents to inhibit protein kinase C activation by NMDA stimulation (Involved in NMDA toxicity) | 8. Downstream effects from Receptor Activation | 9A. Non-NMDA antagonists (Competitive) |
| MDL 27,266 (Merrill Dow) and triazole-one derivatives | 8a. To decrease phopshatidylinositol metabolism | CNQX, NBQX, YM900, DNQX, PD140532 |
| Monosialogangliosides (eg GM1 of Fidia Corp.) and other ganglioside derivatives LIGA20, LIGA4 (may also effect calcium extrusion via calcium ATPase) | kappa opioid receptor agonist: U50488 (Upjohn) and dynorphan | AMOA (2-amino-3[3-9carboxymethoxyl-5-methoxyisoxazol-4-yl]propionate] |
| | kappa opioid receptor agonist: PD117302, CI-977 | 2-phosphophonoethyl phenylalanine derivatives, i.e. 5-ethyl, 5-methyl, 5-trifluoromethyl |
| | 8b. To decrease hydrogen peroxide and free radical injury, eg antioxidants | |
| | 21-aminosteroid (lazaroids) such as U74500A, U75412E and U74006F | 9B. Non-NMDA Non competitive antagonists |
| | U74389F, FLE26749, Trolox (water soluble alpha tocophenol), 3,5-dialkoxy-4-hydroxy-benzylamines<br>Compounds that generate Nitric Oxide (NO) or other oxidation states of nitrogen monoxide (NO+, NO−) including those listed in the box below<br>Nitroglycerin and derivatives, Sodium Nitroprusside, and other NO generating listed on p. 5 of this table<br>Nitric oxide synthase (NOS) Inhibitors: Arginine analogs including N - mono-methy-L-arginine (NMA); N - amino-L-arginine (NAA); N -nitro-L-arginine (NNA); N -nitro-L-arginine methyl ester; N-iminoethyl-L-ornithine | GYK152466<br><br>Evans Blue |

| Agents Active at Metabotropic Glutamate Receptors | Decrease glutamate release | Drugs to decrease intracellular calcium following glutamate receptor stimulation |
|---|---|---|
| 10a. Blockers of Metabotropic Glutamate Receptors | 11. Agents to decrease glutamate release | 12a. Agents to decrease intracellular cadium release |
| AP3 (2-amino-3-phosphonoprionic acid) | Adenosine, and derivatives, e.g. cyclohexyladenosine CNS1145 | Dantrolene (sodium dantrium); Ryanodine (or ryanodine + caffiene) |
| 10b. Agonists of Metabotropic Glutamate Receptors | | 12b. Agents Inhibiting Intracellular Calcium-ATPase |
| (1S, 3R)-1-Amino-cyclopentane-1,3-dicarboxylic acid [(1S, 3R)-ACPD], commonly ref as 'trans'-ACPD | Conopeptides: SNX-111, SNX0183, SNX-230<br><br>Omega-Aga-IVA, toxin from venom of funnel web spider<br>Compounds that generate Nitric Oxide (NO) or other oxidation states of nitrogen monoxide (NO+, NO−) including those listed in the box below<br>Nitroglycerin and derivatives, Sodium | Thapsigargin, cyclopiazonic acid, BHQ ([2,5-di-(tert butyl)-1,4-benzohydroquinone; 2,5-di-(tert-butyl)-1,4benzohydroquinone]) |

TABLE 2-continued

Nitroprusside, and other NO generating
listed on p. 5 of this table
Nitric oxide synthase (NOS) Inhibitors:
Arginine analogs including N-mono-
methyl-L-arginine (NMA); N-amino-L-
arginine (NAA); N-nitro-L-arginine
(NNA); N-nitro-L-arginine methyl ester,
N-iminoethyl-L-ornithine
Additional NO-generating
compounds Isosorbide
dinitrate (isordil)
S-nitrosocaptopril
(SnoCap)
Serum albumin coupled to
nitric oxide (SA-NO)
Cathepsin coupled to nitric
oxide (cathepsin-NO)
Tissue plasminogen
activator coupled to
NO (TPA-NO)
SIN-1 (also known as
SIN1 or molsidomine)
Ion-nitrosyl complexes (e.g.,
nitrosyl-iron complexes,
with iron in the Fe2+ state)
Nicorandil

TABLE 3

Antagonists of the Voltage Dependent Calcium Channels (N, L, T, P and other types)

dihydropyridines (e.g., nimodipine)
phenylalkylamines (e.g., verapamil, (S)-emopamil, D-600, D-888)
benzothiazepines (e.g., diltiazem and others)
bepridil and related drugs
diphenylbutylpiperdines
diphenylpiperazines (e.g., flunarizine/cinnarizine series)
HOE 166 and related drugs
fluspirilene and related drugs
toxins and natural compounds (e.g., snail toxins -
    ωconotoxin GVIA and GVIIA, maitotoxin, taicatoxin,
    tetrandine, hololena toxin, plectreurys toxin,
    funnel-web spider venom and its toxin fraction,
    agatoxins including ω-agatoxin IIIA and ω-agatoxin
    IVA.

TABLE 4

DIHYDROPYRIDINE CALCIUM CHANNEL ANTAGONISTS

| | |
|---|---|
| nifedipine | KW3049 |
| niludipine | oxodipine |
| PY108-068 (darodipine) | CD349 |
| mesudipine | TC81 |
| GX 1048 | YM-09730-5 or (4S) DHP |
| floridine | MDL72567 |
| nitrendipine | Ro18-3981 |
| nisoldipine | DHP-218 |
| nimodipine | nilvadipine |
| nicardipine | amlodipine |
| felodipine | 8363-S |
| PN200-110 (Isradipine) | iodipine |
| CV4093 | azidopine |

TABLE 5

OTHER CALCIUM CHANNEL ANTAGONISTS

| | |
|---|---|
| diclofurime | D-600 |
| pimozide | D-888 |
| prenylamine | Smith Kline 9512 |
| fendiline | ranolzine |
| perhexiline | lidoflazine |
| mioflazine | CERM-11956 |
| flunarizine/cinnarizine | R-58735 |
| series | R-56865 |
| verapamil | amiloride |
| dilfiazine | phenytoin |
| dipropervine | thioridazine |
| (S)-emopamil | tricyclic antidepressants |

In vitro Neuronal Cell Death Assay

An antagonist may be tested for utility in the method of the invention by monitoring neuronal cell death in retinal ganglion cells incubated in vitro with glutamate. The ability of the antagonist to reduce neuronal cell death is determined by scoring live cells which have been incubated overnight with both glutamate and the drug.

Retinal ganglion cells from postnatal rats are identified and their viability ascertained as follows. Under general anesthesia, the fluorescent dye granular blue (Mackromolekulare Chemic, Umstadt, FRG) is injected as approximately a 2% (w/v) suspension in saline into the superior colliculus of 4- to 7-day-old Long Evans rats (Charles River Laboratory, Wilmington, Mass). Two to 7 days later, the animals are killed by decapitation and enucleated, and the retinas quickly removed. The retinas are then dissociated and cultured in Eagle's minimum essential medium (MEM, catalog #1090, Gibco Grand Island, N.Y.), supplemented with 0.7% (w/v) methylcellulose, 2 mM glutamine, 1 μg/ml gentamicin, 16 mM dextrose, and 5%(v/v) rat serum, as described in Lipton et al., *J. Physiol.,* 385:361, (1987) (except that when using a [$Ca^{++}$] of 3 mM or higher—the level found in the vitreous—$Mg^{++}$ was omitted to enhance NMDA receptor-mediated neurotoxicity—see, Levy et al. *Neurology,* 40:852–855

(1990); Hahn et al. *Proc. Nat'l Acad. Sci. USA*, 85:6556–6560 (1988). The cells are plated onto 75 mm² glass coverslips coated with poly-L-lysine in 35 mm tissue culture dishes; glutamate is then added. Sibling cultures receive various doses of NMDA receptor-channel complex antagonists, or non-NMDA antagonists with and without glutamate (e. g., 25 μM).

Cell survival is assayed after one day in culture at 37° C. in an atmosphere of 5% $CO_2$/95% air. Ganglion cells can be unequivocally identified by the continued presence of the fluorescent blue dye. The ability of retinal ganglion cells to take up and cleave fluorescein diacetate to fluorescein is used as an index of their viability as described in detail in Hahn et al., supra. Dye uptake and cleavage correlates well with normal electrophysiological properties assayed with patch electrodes.

To perform the viability test, the cell-culture medium is exchanged for physiological saline containing 0.0005% fluorescein diacetate for 15–45 s, and then cells are rinsed in saline. Retinal ganglion cells that do not contain the fluorescein dye (and thus are not living) often remain visible under both phase-contrast and UV fluorescence optics, the latter because of the continued presence of the marker dye granular blue; other dead retinal ganglion cells disintegrate and only debris remains. In contrast, the viable retinal ganglion cells display not only a blue color in the UV light but also a yellow-green fluorescence with filters appropriate for fluorescein. Thus, the use of two exchangeable fluorescence filter sets permits the rapid determination of the number of viable ganglion cells in the cultures, which are found as solitary neurons or lying among other cells in small clusters (usually in the ratio of approximately 1:10 solitary to clustered). Statistical analyses consisting of a one-way analysis of variance followed by a Scheffe multiple comparison of means is then conducted to determine the effectiveness of drugs such as the NMDA antagonists and/or non-NMDA antagonists in preventing glutamate excitotoxicity.

Use

An effective receptor antagonist will cause a decrease in glaucoma-associated retinal ganglion cell damage or death. As described above, the preferred compounds which cross the blood-brain and blood retinal barriers are preferably administered topically or orally in known, physiologically acceptable vehicles including tablets, liquid excipients and suspensions. Those skilled in the art will appreciate how to formulate acceptable therapeutics.

Antagonists may be compounded into a pharmaceutical preparation, using pharmaceutical compounds well-known in the art; the exact formulation and dosage of the antagonist compound depends upon the route of administration. Generally, the effective daily dose of the antagonists will range from 0.01 to 1000 mg/kg.

Other Embodiments

Other embodiments are within the following claims. For example, the method of the invention may be used for treatment of retinal ganglion cell damage associated with glaucoma in combination with other modes of treatment, e.g., those that are directed to reducing intraocular pressure such as those described herein. In the method of the invention, a useful compound may be administered by any means that allows the compound access to the retinal ganglion cells whose axons comprise the optic nerve. The compounds useful in the method include antagonists of excitatory amino acid receptors (both NMDA and non-NMDA subtypes) that act to reduce retinal ganglion cell neuronal injury via the glaucoma mediated rise in extracellular glutamate, or which reduce binding of glutamate to the NMDA receptor. The antagonists can act to prevent cell death by acting at a modulatory site or a co-agonist site, or by blocking the chain of events initiated by receptor activation.

Other embodiments are within the following claims.

What is claimed is:

1. A method of treating a human patient to reduce damage to retinal ganglion cells associated with glaucoma, said method comprising systemically or intravitreally administrating to said patient a compound that is an antagonist of NMDA receptor-mediated excitotoxicity, in a concentration effective to cause reduction of said excitotoxicity, said antagonist being capable of crossing the blood brain barrier and the blood retina barrier.

2. A method of treating retinal ganglion cells to reduce glaucoma associated damage in a human patient, said method comprising administering to said patient an antagonist of NMDA receptor-mediated excitotoxicity, in a concentration effective to cause reduction of said excitotoxicity, said antagonist being characterized as an NMDA channel antagonist that operates as i) a competitive NMDA antagonist; ii) an uncompetitive NMDA channel blocker; iii) an antagonist of the glycine site of the NMDA receptor; iv) an antagonist of the polyamine site of the NMDA receptor; or v) an inhibitor of downstream effects of NMDA mediated stimulation.

3. The method of claim 2 wherein said antagonist is capable of crossing the blood-brain barrier and the blood-retina barrier.

4. The method of claim 1 or claim 2, wherein said glaucoma is chronic closed-angle glaucoma.

5. The method of claim 1 or claim 2, wherein said glaucoma is primary open-angle glaucoma.

6. The method of claim 1 or claim 2, wherein said glaucoma is pseudoexfoliation glaucoma.

7. The method of claim 2, said compound being capable of crossing the blood-brain and the blood retina barrier.

8. The method of claim 1 or claim 2, said compound being administered to said patient orally.

9. The method of claim 1 or claim 2, said compound being administered to said patient intravitreally.

* * * * *

UNITED STATES PATENT AND TRADEMARK OFFICE
CERTIFICATE OF CORRECTION

PATENT NO.    : 6,482,854 B1
DATED         : November 19, 2002
INVENTOR(S)   : Stuart A. Lipton, M.D., PH. D.

It is certified that error appears in the above-identified patent and that said Letters Patent is hereby corrected as shown below:

<u>Column 1,</u>
Line 2, please add the following paragraph, -- This invention was made at least in part with government funding (NIH grant HD 29587) and the government has certain rights in this invention. --

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,482,854 B1
DATED        : November 19, 2002
INVENTOR(S)  : Stuart A. Lipton, M.D. Ph.D.

It is certified that error appears in the above-identified patent and that said Letters Patent is hereby corrected as shown below:

<u>Title page,</u>
Item [56], References Cited, OTHER PUBLICATIONS, please add the word -- and -- after "Olney, J. Neuropathology,"; and please delete the word "Opthalmolgy" and replace it with -- Ophthalmology --.

<u>Column 1,</u>
Line 37, please delete the word "Timolo" and replace it with -- Timolol --.

<u>Column 2,</u>
Line 7, following the word "brain", please delete the extra word "brain".

<u>Column 10,</u>
Table 5, please indent the word "series".

<u>Columns 6-9,</u>
Please amend Table 2 as follows:
Entry #1, line 5, please delete "[{3-2" and replace it with -- {[3-(2 --.
Entry #5, line 18, please delete the word "Calmodulia" and replace it with
-- Calmodulin --.
Entry #1, line 5, please delete "[{3-2" and replace it with the word -- {[3-(2 --.
Entry #5, line 18, please delete the word "Calmodulia" and replace it with
-- Calmodulin --.
Entry #8b, line 16, please delete "methy" and replace it with -- methyl --.
Entry #9a, line 5, please delete "methoxyisoxazol" and replace it with
-- methoxylisoxazol --.
Entry #11, line 6, please delete "SNX0183" and replace it with -- SNX-183 --.
Entry #12a, line 1, please delete "cadium" and replace it with -- calcium --.

Signed and Sealed this

Seventh Day of October, 2003

JAMES E. ROGAN
*Director of the United States Patent and Trademark Office*